United States Patent [19]

Welker

[11] Patent Number: 4,459,865
[45] Date of Patent: Jul. 17, 1984

[54] CONSTANT PRESSURE CYLINDER WITH VORTEX MIXER

[75] Inventor: Brian H. Welker, Sugar Land, Tex.

[73] Assignee: Welker Engineering Company, Sugar Land, Tex.

[21] Appl. No.: 460,481

[22] Filed: Jan. 24, 1983

[51] Int. Cl.$^3$ .......................... G01N 1/10; G01N 1/14
[52] U.S. Cl. .............. 73/864.62; 73/864.91; 73/DIG. 5
[58] Field of Search ......... 73/864.62, 864.91, DIG. 5; 366/129, 240, 219; 222/226, 229, 239, 243

[56] References Cited

U.S. PATENT DOCUMENTS

| | | | |
|---|---|---|---|
| 2,342,561 | 2/1944 | Trevaskis | 73/432 R |
| 2,636,387 | 4/1953 | McKinney | 73/864.34 |
| 2,660,719 | 11/1953 | Stromberg | 116/204 |
| 3,390,580 | 7/1968 | Taylor | 73/864.34 |
| 3,429,291 | 2/1969 | Hoffman | 116/267 |
| 3,789,670 | 2/1974 | Rosenwald | 73/864.62 |
| 3,793,886 | 2/1974 | Rosenwald | 73/864.62 |
| 3,793,888 | 2/1974 | Rosenwald | 73/864.62 |

Primary Examiner—S. Clement Swisher
Assistant Examiner—Anna M. Schrichte
Attorney, Agent, or Firm—Gunn, Lee & Jackson

[57] ABSTRACT

In the preferred and illustrated embodiment of the disclosed apparatus, a constant pressure cylinder is set forth. Improvements included therewith are a vortex mixer for mixing the accumulated sample or specimen therein. The mixer is slidably mounted on a stainless steel centered rod to avoid damage to the cylinder wall surrounding said vortex mixer. The vortex mixer is slidably mounted on an elongate rod centered and aligned in the cylinder. Moreover, the device additionally incorporates a clear acrylic tracker tube receiving a piston tracker magnetically attracted to the piston for indicating to an observer the elevation of the piston in the constant pressure cylinder.

9 Claims, 3 Drawing Figures

CONSTANT PRESSURE CYLINDER WITH VORTEX MIXER

BACKGROUND OF THE DISCLOSURE

This disclosure sets forth a constant pressure cylinder capable of mixing stored sample or specimen therein. It is desirable to accumulate sample in a vessel at relatively high pressures. The pressure of the vessel is relatively high for the express purpose of confining the sample, and in particular, to prevent the sample from changing phase from a liquid to gas. The device is able to be filled with sample to a maximum design capacity for the device, typically several hundred cubic centimeters. Pressure as high as 2,000 psi are not an extreme.

While the sample is being stored, the sample typically will stratify. After several days or weeks to the time of removal of the sample from the constant pressure cylinder, it is necessary to mix the sample. This disclosure features a vortex mixer. The vortex mixer is in the form of a slidably mounted solid disc (diamond shaped in longitudinal cross-section) which churns the stored sample and thereby mixes it. It is shaped with conic upper and lower faces. The piston is conic on the upper and lower faces to nest with the vortex mixer. This cooperation with adjacent components conveniently enables the vortex mixer to take the illustrated form. Alternate forms are potentially useful.

This mixer and piston conformance enables the piston to be initially forced by pressure at the time of charging to the extreme of its travel, capturing the vortex mixer and nesting against the head at the end of the storage cylinder. This design captures the mixing element. The mixing element is not permitted to float free in the chamber either before or after filling. Free floating mixing elements are dangerous in that they are shakened violently at the time of mixing, and such mixing elements may damage the surface finish on the wall of the surrounding cylinder. The piston slides along the cylinder, thereby requiring a high quality surface finish. The high quality surface finish must be preserved to avoid leakage around the piston at the periphery of the piston. The constrained vortex mixer element is desirable because constraint prevents damage to the highly machined internal face of the cylinder.

This apparatus is advanced over the devices known heretofore in that it includes a visible magnetic indicator. There is a clear acrylic tube mounted along the exterior. A magnet is positioned in the tube, and for sake of identification, the magnet is color coded. The magnet is coupled through the wall of the cylinder. Preferably, the cylinder is made of stainless steel to enable the magnet on the exterior to couple with a cooperative magnet on the piston thereby forming a visible indication of the elevation of the piston within the cylinder.

Devices having a bearing on the present disclosure include a Qwik Site sample vessel sold by Y-Z Industries of Snyder, Tex. That device uses an untethered round ball as a vortex mixer. The indicator for the position of the piston is a set of orange and white flags which are flipped to indicate piston position by a change of color. Another device of interest is U.S. Pat. No. 3,789,670 of Rosenwald. The same inventor is listed on additional U.S. Pat. Nos. 3,793,886 and 3,793,888. The earlier patent of McKinney U.S. Pat. No. 2,636,387 is also noted. An additional reference is U.S. Pat. No. 3,390,580 of Taylor. The references listed above are representative of devices over which the present apparatus distinguishes. In summary, such references do not set forth a device of the nature generally summarized above.

This apparatus is therefore an improved constant pressure cylinder for storage of a sample. It is improved by incorporation of a vortex mixer slidably mounted on an axially positioned rod through the apparatus. The structure further incorporates an externally located clear acrylic tubing. The tubing receives a magnet therein to serve as a marker, the magnet tracking the position of the piston within the cylinder. The piston moves as the sample accumulates, thereby indicating to an observer the position of the piston and the volume of sample stored in the device.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figures 1, 2, 3:
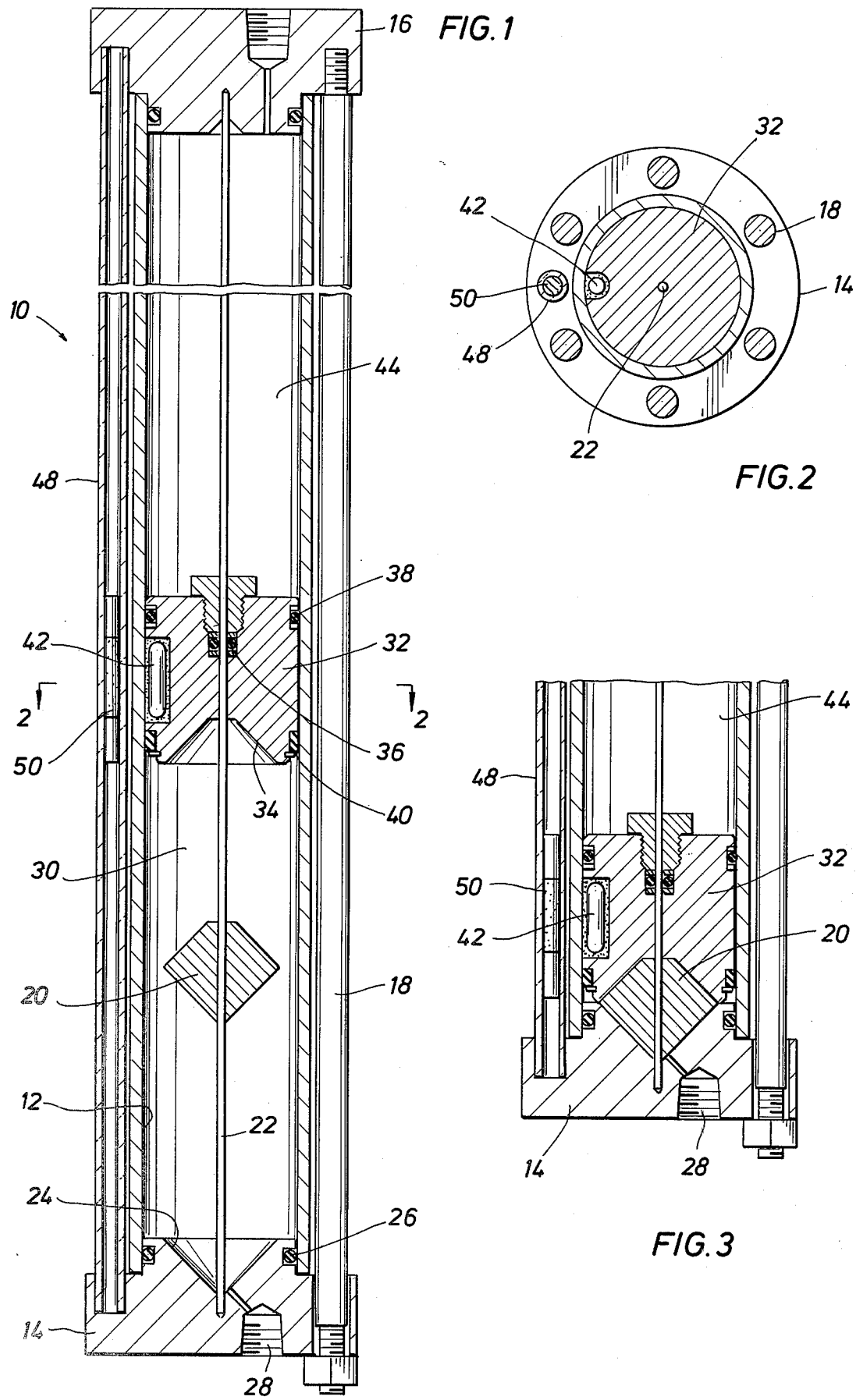
FIG. 1 is a sectional view through the improved constant pressure cylinder and piston constructed in accordance with the teachings of the present disclosure.
FIG. 2 is a sectional view taken along the line 2—2 of FIG. 1 showing details of construction of the piston and the indicator apparatus visible on the exterior.
FIG. 3 is a view showing the position of the piston, vortex mixer and lower head when the piston moves to the bottom most position.

Attention is first directed to FIG. 1 of the drawing. There, a constant pressure cylinder 10 is comprised of an outer cylindrical sleeve 12. It extends between a lower head 14 and similar or matching head 16 at the upper end. The two heads are constructed with surrounding flanges. This enables them to receive tie bolts 18 extending the full length of the apparatus and surrounding the cylinder 12. The two heads are pulled toward one another, and flange plates extending therebeyond define seals around the edges of the cylindrical sleeve 12 to prevent leakage.

The head 14 has an internal face conforming in shape with the lower face of a slidably mounted vortex mixer 20. The mixer 20 is shown in sectional view to have a lower face which is conic. It is axially drilled, enabling it to fit on a mounting rod 22. The rod 22 is concentric within the cylinder. The rod 22 extends into the head 14 adjacent to a conic or dished face 24. This face conforms to the nether face on the vortex mixer. The vortex mixer thus nests the lower head in a manner shown better in FIG. 3 as will be described.

The lower head is further constructed with a groove for receiving an O-ring 26 on the interior of the cylindrical sleeve. The lower head is additionally drilled at 28, this providing a means for threaded connection of a conduit thereby delivering fluid flow into the cylinder to be stored. There is a lower storage chamber identified by the numeral 30. This chamber is above the head 14 and below the piston 32. The piston 32 has a conformed lower face 34 which also nests against the vortex mixer. The piston is slidably mounted to travel along the rod 22. Suitable seals are incorporated at 36 to prevent leakage along the guide rod 22. The piston 32 is constructed with a surrounding peripheral seal rings 38 at the top and 40 at the bottom. The seal construction can be identical or different, and in this instance, they are shown to be different. The two seals prevent leakage along the exterior of the piston 32. The piston 32 is formed of stainless steel, and the cylinder 12 is preferably formed of stainless. The two stainless components enable the use of a magnet 42 received in a cavity cut in the side of the piston (between the seals). The magnet 42 is mounted with epoxy or some other suitable adhesive in a side-located cavity between the seal rings. The magnet is able to achieve magnetic attraction through the wall of the cylinder 12 as will be described.

The piston 32 divides the device into upper and lower chambers. The lower chamber is identified by the numeral 30 and the upper chamber is identified at 44. The chamber 44 is located below the upper head 16. The upper head 16 is constructed substantially identical to the lower head in terms of mounting, and they differ only slightly in details of the exposed faces. The chamber 44 is adapted to be precharged. Typically, an inert gas is charged in the chamber 44. The inert gas enables the device to sustain a fixed back pressure. That is, the sample is accumulated and stored against a fixed back pressure. Assume as an example that the chamber 44 is precharged with an initial pressure of 1,000 psi. At the time the chamber 44 is charged, the chamber 30 approaches zero volume. This occurs when the piston is forced to the bottom of its possible travel range. The piston is driven down by the precharge of gas, say at 1,000 psi. As sample is accumulated, the piston is forced off the lower head and is moved upwardly against pressure. The upper chamber shrinks as the gas cushion is forced from it as sample is accumulated in the lower chamber. The upper chamber is initially filled with inert gas and is reduced thereafter as sample filling occurs. The pressure is allowed to climb as volume diminishes; or in most cases, a manual valve is used to bleed off excess pressure. A relief valve is also an option.

The present apparatus further includes a clear acrylic tube 48. The tube 48 is parallel to the cylinder 12. The tube 48 has an internal diameter sized to receive a slidably positioned magnet 50. The magnet 50 is marked with color codes or the like. The magnet 50 attracts the magnet 42. The magnet 50 is able to follow the piston because it is magnetically coupled to the magnet 42. The magnet 50 is frictionally fitted within the clear acrylic tube. The magnet 42 thus attracts the magnet 50 and drags it along the acrylic tube. Preferably, a pad is placed on the magnet 50 with a suitable surface adhesive, and the pad contacts the acrylic tube to sustain a relatively smooth frictional drag. This frictional drag prevents the magnet from sliding too freely. The magnet should be snug, not unduly tight so that it can be pulled by the magnet 42.

The initial condition of the equipment finds the chamber 30 reduced in size. This is better shown in FIG. 3 of the drawings. There, the vortex mixer 20 has been forced to the bottommost position by movement of the piston 32. This is the initial position of the piston and vortex mixer. At this juncture, the chamber 44 has been initially charged with a suitable gas at an elevated pressure. No sample has been introduced into the chamber 30, and the device is then prepared for receipt of sample.

A conduit is connected to the threaded port 28. The conduit introduces sample into the lower chamber. Sample forces the vortex mixer upwardly as sample is introduced beneath the mixing element 20 and that in turn forces the piston 32 upwardly. The vortex mixer will move only fractionally contrasted with the piston 32, and it tends to settle because sample accumulates all around the vortex mixer 20. In fact, the mixer typically simply rests on the lower head 14. The piston is eventually forced to the top end of its travel. As it travels, the magnet 42 attracts the externally located indicator magnet 50, forming a visible indication of the elevation of the piston. If desired, the clear acrylic tubing 48 can be color coded with dots, numbers or other symbols to indicate the extremities of movement and to provide gradations of location in between. This is a matter of convenience to the user. It will be observed that the piston 32 moves upwardly forcing compressed inert gas from the chamber 44. Sample collects beneath the piston without leakage into the upper chamber. Rather, the seals which surround the piston prevent leakage both along the cylinder wall; leakage along the guide rod 22 is prevented by the seals 36.

The device is installed when the lower chamber 30 is empty of sample. It is removed after it has been filled to some desired level, even to the point where the upper chamber 44 is reduced substantially to zero by expelling the compressed gas. At the time of removal, the device is typically carried to a testing laboratory where the sample is tested. At the time of removal, clear indication with a relative high degree of accuracy of the volume of sample within the chamber 30 is simply noted from the position of the indicator magnet 50. In the laboratory, the device is discharged to deliver the sample. Typically, the sample is used to determine where the price of chemicals or petroleum products by an assay of the sample.

Removal is accomplished by first mixing the sample. Sample stratification is a problem. Sample stratification typically will occur especially of the sample is collected over a period of days or weeks. Sample stratification may distort the report obtained from the assay. To avoid this, the vortex mixer of the present disclosure is used to churn the sample to break up stratified layers in the sample. The entire cylinder 10 is vigorously shaked, compelling the vortex mixer to slide along the guide rod 22. As it slides, it churns and stirs the stored sample. The mixer breaks up the layers in the sample. The mixer faces are somewhat streamlined in shape and therefore easily slide along the guide rod 22. An important advantage of the apparatus is the fact that the vortex mixer, even while undergoing vigorous shaking, does not bang into the side wall of the cylinder. The cylinder must seal the piston with a high quality seal. The cylinder wall finish typically is achieved at great expense in machining cost. Surface finishes on the internal face of the cylinder must be machined typically by precision techniques including grinding and lapping. The surface finish should ideally be in the range of 2–8 rms, a relatively high quality finish. Should the vortex mixer bang against the wall, the mixer may dent or dimple and thereby damage the surface finish. Therefore, the guide rod fixes the location of the vortex mixer so that it does not contact the side wall. Protection of the side wall is thus accomplished by this mixing and churning apparatus. This prevents damage to the side wall and hence reduces the possibility of a leakage as the piston slides past damaged portions of the side wall.

The foregoing is directed to the preferred embodiment, the scope is determined by the claims which follow.

What is claimed is:

1. A sample storage apparatus comprising:
   (a) an elongate hollow cylinder having cylinder heads at both ends to close said cylinder;
   (b) a piston slidably mounted within said cylinder to divide said cylinder into first and second chambers, one chamber serving to receive a pressurized fluid and the other chamber adapted to receive sample through a passage in one of said cylinder heads and thereby comprising a sample chamber;
   (c) an elongate rod through said sample chamber concentric to said cylinder; and
   (d) a slidably mounted vortex mixing means positioned on said rod for movement along said rod, said vortex means having a size and shape permitting said means to move along said rod without touching the wall of the surrounding cylinder while mixing sample in said sample chamber.

2. The apparatus of claim 1 wherein said vortex mixer means comprises a solid body having a circular edge smaller than said cylinder to fit within said sample chamber, and is, in longitudinal cross section, diamond shaped to define upper and lower conic faces, and having an axial hole therein to enable said vortex mixing means to slide along said elongate rod.

3. The apparatus of claim 1 wherein one of the cylinder heads has a face within said sample chamber, and said face is conformed to said vortex mixing means to enable facial contact and nesting between said vortex mixing means and said cylinder head face.

4. The apparatus of claim 3 wherein said vortex mixer means comprises a solid body having a circular edge smaller than said cylinder to fit within said sample chamber, and is, in longitudinal cross section, diamond shaped to define upper and lower conic faces, and having an axial hole therein to enable said vortex mixing means to slide along said elongate rod.

5. The apparatus of claim 3 including a lower face on said piston in said sample chamber confronting said vortex mixing means, and said lower face conforms to said vortex mixing means and nests thereagainst to enable said piston to move toward said one cylinder head in reducing said sample chamber toward minimum volume which minimum volume is obtained on capturing said vortex mixing means nested between said piston and said one cylinder head.

6. The apparatus of claim 5 wherein said piston supports a magnetically attracted means and including:
   (a) an externally located track means adjacent to said cylinder;
   (b) piston position indicator means supported by said track means, said means further being magnetically coupled to said magnetically attracted means; and
   (c) holding means cooperative with said piston position indicator means and said track means for releasably holding said piston indicator means along said track means.

7. The apparatus of claim 6 wherein
   (a) said track means comprises an elongate hollow transparent tube;
   (b) said piston position indicating means comprises a magnet in said transparent tube;
   (c) said holding means comprises a frictionally engaging surface on said magnet engaging said tube;
   (d) said cylinder heads support said transparent tube parallel to said cylinder;
   (e) said piston includes separate encircling seal rings to prevent leakage around said piston;
   (f) said elongate rod extends through said piston at a seal to prevent leakage along said rod; and
   (g) said vortex mixer means comprises a solid body having a circular edge smaller than said cylinder to fit within said sample chamber, and is, in longitudinal cross section, diamond shaped to define upper and lower conic faces, and having an axial hole therein to enable said vortex mixing means to slide along said elongate rod.

8. A sample storage apparatus comprising:
   (a) an elongate hollow cylinder having cylinder heads at both ends to close said cylinder and having an elongate rod extending axially of said cylinder;
   (b) a piston slidably mounted within said cylinder to divide said cylinder into first and second chambers, one chamber serving to receive a pressurized fluid and the other chamber adapted to receive sample through a passage in one of said cylinder heads and thereby comprising a sample chamber;
   (c) a parallel external track means for supporting a piston position indicator means; and
   (d) means coupling said position indicator means through said cylinder wall with said piston to cause said piston position indicator means to move with said piston;
   (e) said piston position indicator means comprising a magnet magnetically coupled to said piston;
   (f) wherein said piston position indicator means moves with said piston from a first position to a second position to thereby indicate filling of said sample chamber in said cylinder;
   (g) said track means comprises an elongate hollow transparent tube;
   (h) said piston position indicating means comprises a magnet in said transparent tube;
   (i) holding means cooperative with said piston position indicator means and said track means for releasably holding said piston position indicator means along said track means;
   (j) said holding means comprises a frictionally engaging surface on said magnet engaging said tube;
   (k) said cylinder heads support said transparent tube parallel to said cylinder;
   (l) said piston includes separate encircling seal rings to prevent leakage around said piston; and
   (m) said elongate rod extends through said piston at a seal to prevent leakage along said rod.

9. The apparatus of claim 1 wherein said piston supports a magnetically attracted means, and including:
   (a) an externally located track means adjacent to said cylinder;
   (b) piston position indicator means supported by said track means, said means further being magnetically coupled to said magnetically attracted means; and
   (c) holding means cooperative with said piston position indicator means and said track means for releasably holding said piston position indicator means along said track means.

* * * * *